United States Patent
Baer et al.

[11] Patent Number: 5,859,699
[45] Date of Patent: Jan. 12, 1999

[54] LASER CAPTURE MICRODISSECTION ANALYSIS VESSEL

[75] Inventors: Thomas M. Baer, Mountain View; David F. Head, Los Gatos, both of Calif.

[73] Assignee: Arcturus Engineering, Inc., Santa Clara, Calif.

[21] Appl. No.: 797,026

[22] Filed: Feb. 7, 1997

[51] Int. Cl.⁶ ................................................. G01N 1/10
[52] U.S. Cl. .................................................. 356/246
[58] Field of Search ......................... 356/244–246; 428/328, 447, 452, 332, 339; 422/102, 55–58, 61; 436/163, 101, 103, 84, 110, 113

[56] References Cited

U.S. PATENT DOCUMENTS

| | | | |
|---|---|---|---|
| 5,349,436 | 9/1994 | Fisch | 356/246 |
| 5,529,841 | 6/1996 | Neihof | 428/328 |
| 5,574,077 | 11/1996 | Dougherty et al. | 523/137 |
| 5,756,049 | 5/1998 | Brayton | 422/61 |

FOREIGN PATENT DOCUMENTS

| | | | |
|---|---|---|---|
| 1938943 | 11/1971 | Germany . | |
| 0081976 | 6/1983 | United Kingdom | B01L 3/00 |
| WO 95/23960 | 9/1995 | WIPO . | |
| WO 96/40435 | 12/1996 | WIPO . | |
| WO 97/13838 | 4/1997 | WIPO . | |
| WO 97/29354 | 8/1997 | WIPO . | |
| 98/01285 | 1/1998 | WIPO . | |

OTHER PUBLICATIONS

G. Isenberg, et al. "Cell surgery by laser micro–dissection: a preparative method" Journal of Microscopy, vol. 107 pt. 1, pp. 19–24, May 1976.

*Primary Examiner*—Frank G. Font
*Assistant Examiner*—Michael P. Stafira
*Attorney, Agent, or Firm*—D'Alessandro & Ritchie

[57] ABSTRACT

A laser capture microdissection lift-off substrate comprising a transparent thermoplastic film is incorporated into substrate which may take the form of a cap or other structure associated with an analysis vessel or which may be used with a holder or other element of a LCM tissue sample transfer apparatus. The thermoplastic lift-off substrate film is held in a fixed position on the substrate which may be relative to a feature of a biological analysis vessel. The film may be affixed to a substrate which is a structure which goes into the vessel such that the sample is held in a fixed position relative to an observation port on the vessel.

6 Claims, 9 Drawing Sheets

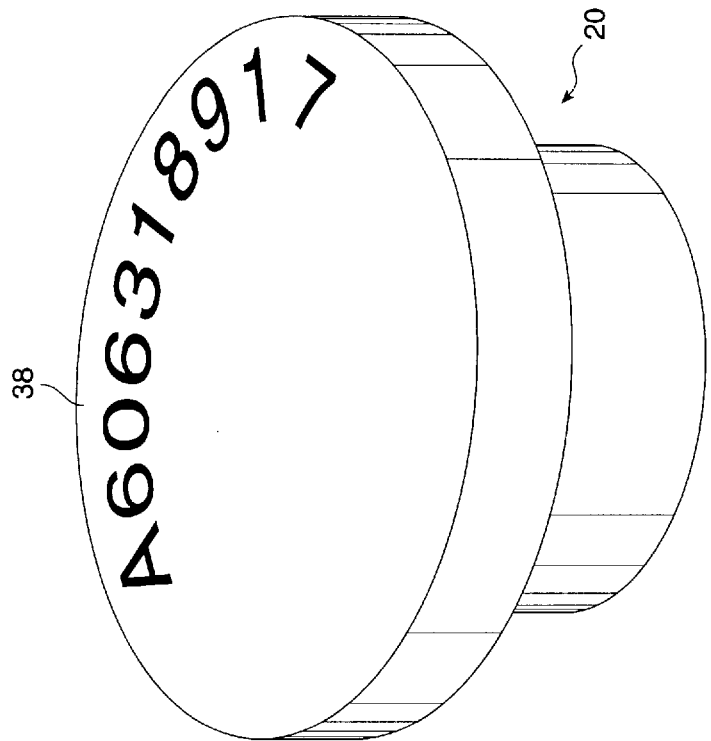
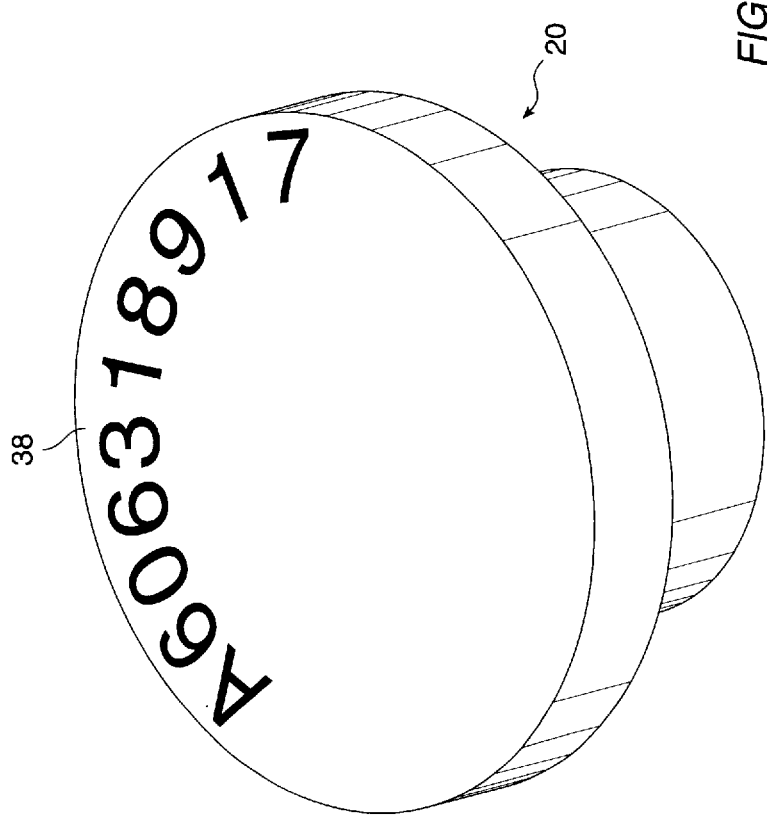
FIG. 6

LASER CAPTURE MICRODISSECTION ANALYSIS VESSEL

BACKGROUND OF THE INVENTION

1. Field of the Invention

The present invention relates to laser capture microdissection. More particularly, the present invention relates to consumables for laser capture microdissection and to liquid reagent vessels for holding transfer films used in laser capture microdissection.

2. The Prior Art

Diseases such as cancer have long been identified by examining tissue biopsies to identify unusual cells. The problem has been that there has been no satisfactory prior-art method to extract the cells of interest from the surrounding tissue. Currently, investigators must attempt to manually extract, or microdissect, cells of interest either by attempting to mechanically isolate them with a manual tool or through a convoluted process of isolating and culturing the cells. Most investigators consider both approaches to be tedious, time-consuming, and inefficient.

A new technique has been developed which can extract a small cluster of cells from a tissue sample in a matter of seconds. The technique is called laser capture microdissection (LCM). Laser capture microdissection is a one-step technique which integrates a standard laboratory microscope with a low-energy laser and a transparent ethylene vinyl acetate polymer thermoplastic film such as is used for the plastic seal in food product packaging.

In laser capture microdissection, the operator looks through a microscope at a tissue biopsy section mounted on a standard glass histopathology slide, which typically contains groups of different types of cells. A thermoplastic film is placed over and in contact with the tissue biopsy section. Upon identifying a group of cells of interest within the tissue section, the operator centers them in a target area of the microscope field and then generates a pulse from a laser such as a carbon dioxide laser having an intensity of about 50 mW and a pulse duration of between about 50 to about 500 mS. The laser pulse causes localized heating of the plastic film as it passes through it, imparting to it an adhesive property. The cells then stick to the localized adhesive area of the plastic tape directly above them, whereupon the cells are immediately extracted and ready for analysis. Because of the small diameter of the laser beam, extremely small cell clusters may be microdissected from a tissue section.

By taking only these target cells directly from the tissue sample, scientists can immediately analyze the gene and enzyme activity of the target cells using other research tools. Such procedures as polymerase chain reaction amplification of DNA and RNA, and enzyme recovery from the tissue sample have been demonstrated. No limitations have been reported in the ability to amplify DNA or RNA from tumor cells extracted with laser capture microdissection.

Laser capture microdissection has successfully extracted cells in all tissues in which it has been tested. These include kidney glomeruli, in situ breast carcinoma, atypical ductal hyperplasia of the breast, prostatic interepithielial neoplasia, and lymphoid follicles. The direct access to cells provided by laser capture microdissection will likely lead to a revolution in the understanding of the molecular basis of cancer and other diseases, helping to lay the groundwork for earlier and more precise disease detection.

Another likely role for the technique is in recording the patterns of gene expression in various cell types, an emerging issue in medical research. For instance, the National Cancer Institute's Cancer Genome Anatomy Project (CGAP) is attempting to define the patterns of gene expression in normal, precancerous, and malignant cells. In projects such as CGAP, laser capture microdissection is a valuable tool for procuring pure cell samples from tissue samples.

Laser capture microdissection, like all emerging techniques, still has room for improvement. With further refinement of the plastic film and activation by a more tightly focussed laser beam, the technique of extraction of single cells can easily be foreseen.

It is therefore an object of the present invention to provide a liquid reagent biological analysis vessel which will facilitate laser capture microdissection analysis.

It is another object of the present invention to provide a liquid reagent biological analysis vessel for use with laser capture microdissection analysis which allows greater automation of the analysis process.

Yet another object of the present invention is to provide a liquid reagent biological analysis vessel for use with laser capture microdissection analysis which is less susceptible to DNA contamination than is presently encountered.

BRIEF DESCRIPTION OF THE INVENTION

Designs for laser capture microdissection consumables according to the present invention involve incorporating a laser capture microdissection lift-off substrate comprising a transparent thermoplastic film onto a substrate. The substrate may be, for example a cap or other structure which may be associated with an analysis vessel such as an epindorf tube.

According to its broadest aspect, the present invention comprises any method to hold a thermoplastic lift-off substrate film in a fixed position relative to a biological analysis vessel. For example, the film may be affixed to a structure which is inserted into the vessel and is held therein such that the sample is held in a fixed position relative to an observation port on the vessel.

Because analysis of cells dissected from samples using the laser capture microdissection process employs small volumes of liquid reagents such as proteinase solutions, the sample is held in a fixed position relative to the observation port of the vessel so that it may be verified that the tissue sample has been immersed in the liquid reagent.

In the simplest embodiments of the present invention, the present invention comprises a cap for the analysis vessel. The cap is formed from a machined or injection molded material such as plexiglas, and includes a window for holding the lift-off substrate film. If the cap is formed from a transparent material, the film may be disposed upon a window portion of the cap. The film may also be disposed across an aperture formed in the cap with the laser propagating through the aperture in the cap.

According to a first embodiment of the present invention, an aperture is disposed through the cap of an analysis vessel, such as an epindorf tube. A thermoplastic lift-off substrate film is fastened across the aperture by gluing, by welding the thermoplastic around the periphery of the aperture or by some other known fastening means which holds the film in place. The film itself acts as a transparent window that allows for inspection of the lifted tissue sample.

To perform the laser capture microdissection, the cap and film assembly is placed in a suitable holder in the laser capture microdissection apparatus and is aligned in contact with the slide containing the tissue sample. The operator then centers the cells of interest on the laser beam target and then activates the laser pulse to weld the selected cell group to the film.

After welding the tissue sample of interest to the film affixed to the cap, a small volume of proteinase solution is placed in the ependorf tube, the cap is placed on the epindorf tube and the tube is inverted. The tissue is dissolved and the DNA is free to enter the solution. The solution is then pipetted out of the tube and into the PCR mixture for analysis. The positioning of the film over the through hole permits inspection to insure that the sample has been dissolved.

According to a second embodiment of the present invention, the cap comprises a solid piece having transparent optical quality windows on its top and bottom surfaces. The film is deposited or otherwise affixed to the surface of the bottom window of the cap using a process such as spin coating, dipping or spraying. The tissue is then welded to the top of the cap as described for the first embodiment with the laser propagating through the optical windows on the cap.

The vessel may be the well known ependorf tube, but persons of ordinary skill in the art will appreciate that the techniques described herein may be used for caps that are configured to fit other standard biological fluid analysis sample holders such as 96 well microtiter plates.

According to a third embodiment of the present invention, the LCM transfer film is affixed to a disk or plug which may be inserted into the analysis vessel.

According to the present invention, if it is desired to combine more than one tissue sample in a single analysis vessel, a first tissue sample is dissolved in the vessel. The first cap, disk, or plug is then removed from the analysis vessel and a second cap, disk, or plug is then inserted into the vessel. In this manner, more than one tissue sample may be easily combined in a single analysis vessel

BRIEF DESCRIPTION OF THE DRAWING FIGURES

FIGS. 1a, and 1b are side and top views, respectively, of a cap for an analysis vessel including a LCM transfer film according to a first embodiment of the present invention.

FIG. 6 is a perspective view of a cap for an analysis vessel including an identifying serial number according to another aspect of the present invention.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Figure 1A:
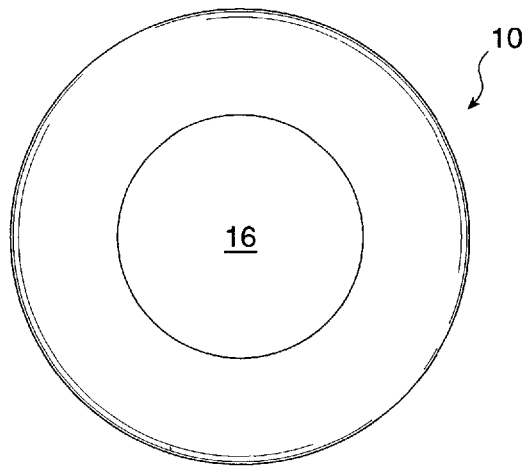
Figure 1B:
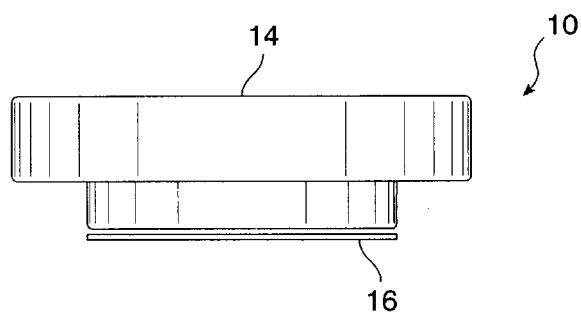
Figure 2:
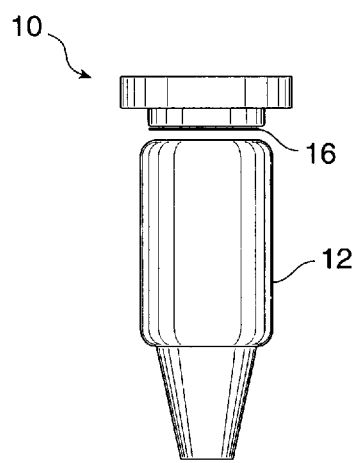
FIG. 2 is a side view of an analysis vessel positioned to mate with the cap of FIGS. 1a and 1b.

Referring first to FIGS. 1a and 1b, side and top views, respectively, are presented of a cap 10 for an analysis vessel including a LCM transfer film according to a first embodiment of the present invention. FIG. 2 shows Cap 10 positioned to mate with analysis vessel 12, which may be, for example, an eppindorf tube.

Cap 10 may be formed from a material such as machined or die cast plexiglas, and includes an aperture 14 formed therethrough and a LCM transfer film layer 16, which may be formed from a thermoplastic film material such as ethylene vinyl acetate (EVA) polymer, is attached to cap 10 covering aperture 14. LCM transfer film 16 may be fastened to the surface of the underside of cap 10 by various known fastening means. Such films for LCM application have thicknesses typically in the range of from about 10 to about 500 microns.

The thermoplastic film is preferably a 100 micron thick ethyl vinyl acetate (EVA) film available from Electroseal Corporation of Pompton Lakes, N.J. (type E540). The film is chosen to have a low melting point of about 90° C. This particular EVA film has been doped with an infrared napthalocyanine dye, available from Aldrich Chemical Company (dye number 43296-2 or 39317-7). These dyes were chosen because they have a strong absorption in the 800 nm region, a wavelength region that overlaps with an high power AlGaAs laser diode (model OPCAOO1-808FC available from Opto Power Corporation, Tucson Ariz.) which is used to selectively melt the film. The dye is mixed with the melted bulk plastic at a temperature of about 120 C. The dyed plastic is then manufactured into a film using standard film manufacturing techniques. The dye concentration in the plastic is about 0.001M.

As may be seen most easily from an examination of FIG. 1b, aperture 14 provides an unobstructed view of LCM transfer film 16 through the body of cap 10. According to the present invention, a tissue sample may be attached to LCM transfer film 16 by placing the cap 10 over the slide containing the sample and generating a laser pulse as is known to perform laser capture microdissection. Cap 10, with the captured tissue sample, may then be mated with analysis vessel 12.

After the cap 10 has been mated with analysis vessel 12, aperture 14 provides a convenient way to observe the sample in analysis vessel 12. This is particularly useful for procedures in which the sample is to be dissolved by a small volume of proteinase solution placed in the vessel 12. Aperture 14 permits observation of whether the sample has contacted the solution and has been dissolved.

Figure 3A:
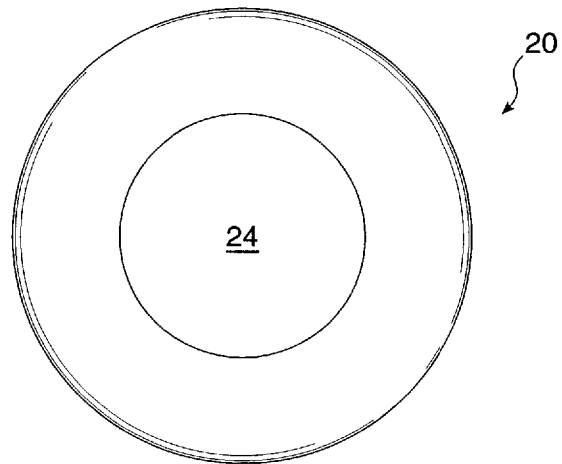
FIGS. 3a and 3b are side and top views, respectively, of a cap for an analysis vessel including a LCM transfer film according to a second embodiment of the present invention.
Figure 3B:
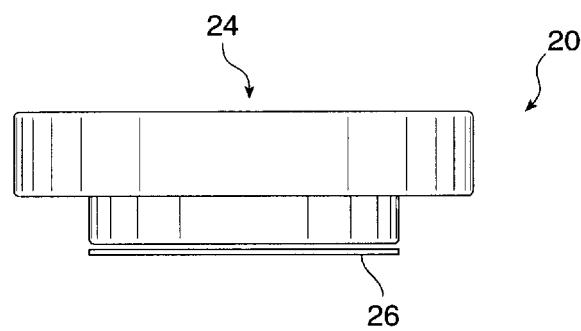
Figure 4:
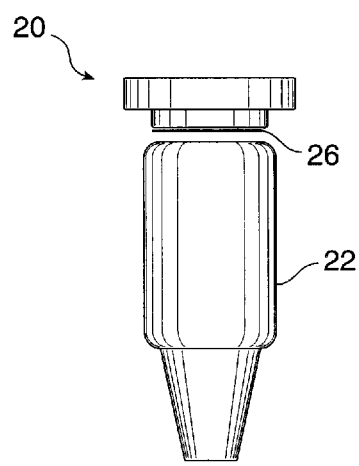
FIG. 4 is a side view of an analysis vessel positioned to mate with the cap of FIGS. 3a and 3b.

Referring now to FIGS. 3a and 3b are side and top views, respectively, are shown of a cap 20 for an analysis vessel including a LCM transfer film according to a second embodiment of the present invention. FIG. 4 is a side view of an analysis vessel 22 positioned to mate with the cap of FIGS. 3a and 3b, which may be, for example, an epindorf tube.

Cap 20 includes an optical window 24 through its body and a layer of LCM transfer film 26 disposed over the surface of optical window 24 at the underside of the cap 20. If cap 20 is made from a material such as plexiglas, window 24 is easily formed by controlling the surface characteristics of the cap as is known in the art. LCM transfer film 24 may be affixed to the window surface of the underside of cap 20 using various known fastening techniques.

As with the aperture 14 of the embodiment of FIGS. 1a and 1b, window 24 provides an unobstructed view of LCM transfer film 26 through the body of cap 20. As with the embodiment of FIGS. 1a and 1b, a tissue sample may be attached to LCM transfer film 24 by placing the cap 20 over the slide containing the sample and generating a laser pulse to perform laser capture microdissection. Cap 20, with its captured tissue sample, may be mated with analysis vessel 22.

After the cap 20 has been mated with analysis vessel 22, window 24 provides a convenient way to observe the sample in analysis vessel 22. This is particularly useful for procedures in which the sample is to be dissolved by a small volume of proteinase solution placed in the vessel 22 since window 24 permits observation of whether the sample has contacted the solution and has been dissolved.

Figure 5:
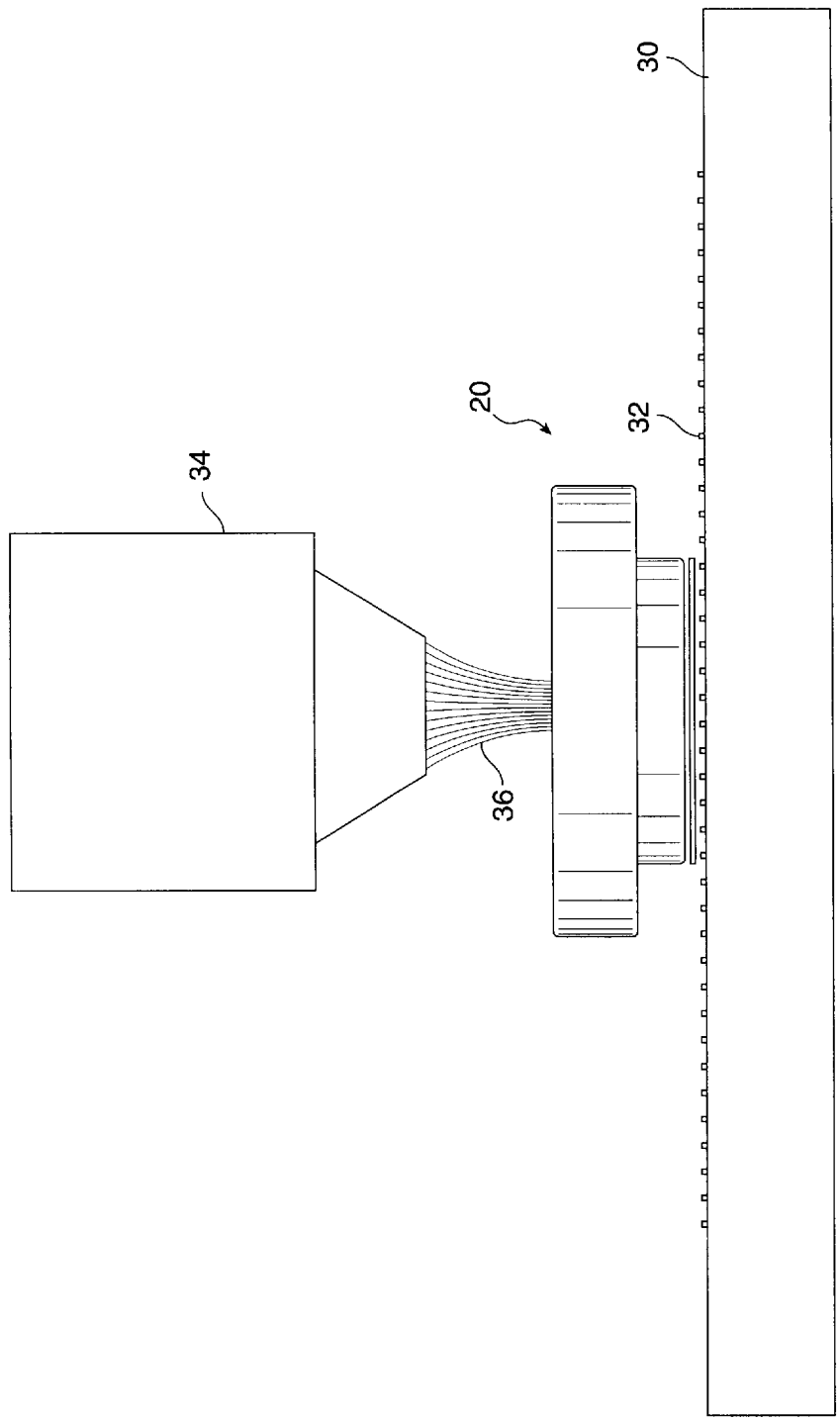
FIG. 5 is a side view of an analysis vessel cap according to the present invention shown positioned over a glass slide and tissue sample and placed under a microscope objective, illustrating a laser capture microdissection procedure.

FIG. 5 is a side view of an analysis vessel cap 20 according to the present invention shown positioned over a glass slide 30 and tissue sample 32. The slide 30 and cap 20 are placed under a microscope objective 34, and a laser pulse, shown diagrammatically at reference numeral 36 is directed at a selected region 36 of the tissue sample 32 to perform laser capture microdissection of the tissue sample 32. FIG. 5 illustrates the ease of use of the present invention, since the integral cap and LCM transfer film assembly is easily handled, either manually or by automated means, and thus greatly facilitates obtaining the LCM sample and decreases the possibility of DNA contamination of the sample during handling and transport. Those of ordinary skill in the art will appreciate that an alternate configuration which may be employed is an inverted microscope wherein the tissue sample may be viewed from underneath the sample slide. Such skilled persons will appreciate that the present invention may easily be used in such a configuration.

According to another aspect of the present invention, the cap of FIGS. 1a and 1b and 3a and 3b may be provided with an identifying serial number. FIG. 6 is a perspective view of a cap 20 for an analysis vessel including an identifying serial number 38 according to this aspect of the present invention.

As an example of this aspect of the present invention, cap 20 is equipped with a marking means 38 such as a UPC label or laser etched label. Serializing all of the caps provides for easy identification and tracking of cell samples. The label may be read by a sensor, such as a UPC label sensor or OCR sensor which is mounted in or on the laser capture microdissection apparatus.

According to this aspect of the present invention, the serial number 38 is placed on the top of the cap. Placing the serial number on the top of cap 20, and the thickness of cap 20 is selected to be larger than the depth of field of the microscope objective. Thus, the microscope can be focussed on the tissue sample below the bottom surface of the cap and not have the label or serial number interfere optically, since the label is far from the focal plane of the imaging lens and is thus out of focus.

Figure 7:
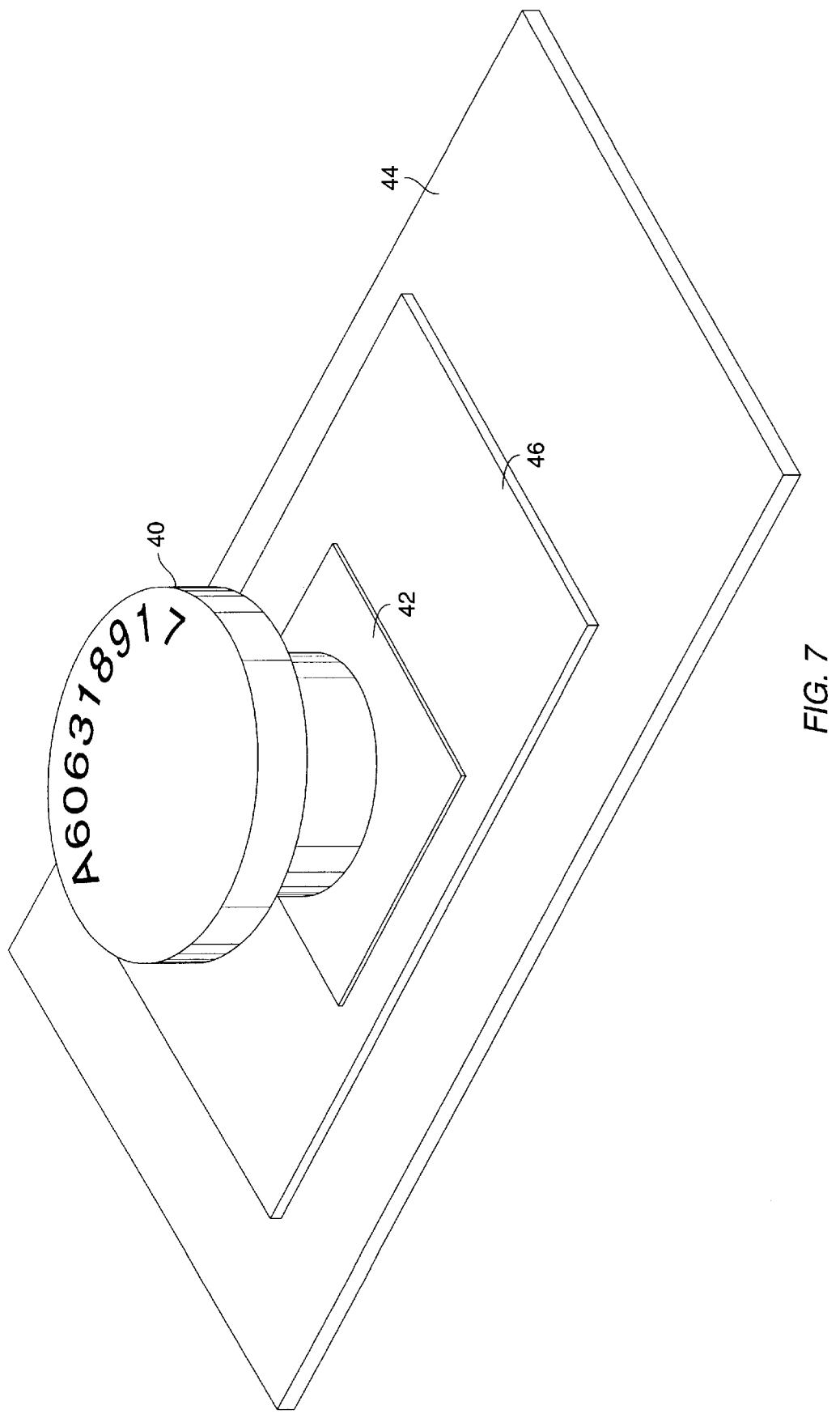
FIG. 7 is a perspective view of a cap for an analysis vessel showing a procedure for affixing the LCM film thereto.

There are several ways in which the LCM transfer film may be affixed to the surface of the caps according to the present invention. FIG. 7 is a perspective view of a cap 40 for an analysis vessel illustrating a step in a first procedure for affixing the LCM film thereto.

First, a small, e.g., about 1 cm square piece of EVA film 42 is cut. The film 42 is gently pressed onto the bottom surface of the cap 40 making it stick thereto. A glass microscope slide 44 is heated to about 100 C on a hot plate. A 0.002 inch thick piece of mylar plastic release liner 46 is placed on the slide. As is known in the art, a release liner is a plastic sheet that is coated with a silicone coating so it does not stick to the EVA film material or the glass slide.

The cap 40 with its attached film 42 is pressed onto the release liner/slide assembly for about 5 seconds or until the film melts. The cap 40 with attached film 42 and release liner 46 is then removed from the hot glass slide 44, cooled down to room temperature, and the release liner 46 is peeled off. Finally, the excess EVA film is trimmed off.

Figure 8:
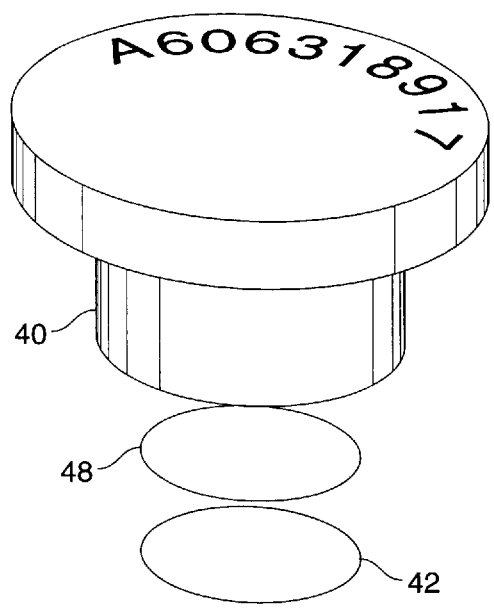
FIG. 8 is a perspective view of a cap for an analysis vessel showing an alternate procedure for affixing the LCM film thereto.

FIG. 8 is a perspective view of a cap for an analysis vessel showing an alternate procedure for affixing the LCM film thereto. According to this method, a piece of transparent double sided adhesive tape 48 (such as standard double stick tape available from 3M Corporation) may be used to tape the EVA film 42 to the bottom of the cap 40. The excess EVA film may then be trimmed off.

As will be appreciated by those of ordinary skill in the art from an examination of the disclosure, the present invention involves holding the LCM transfer film in a fixed position relative to a biological analysis vessel. In addition to the vessel cap embodiments of FIGS. 1a and 1b and 3a and 3b, other embodiments of the present invention are contemplated herein. In general, the LCM transfer film may be affixed to something that may be placed into the vessel such that the film and its adhered tissue sample is held in a fixed position relative to an observation port on the vessel.

Figure 9:
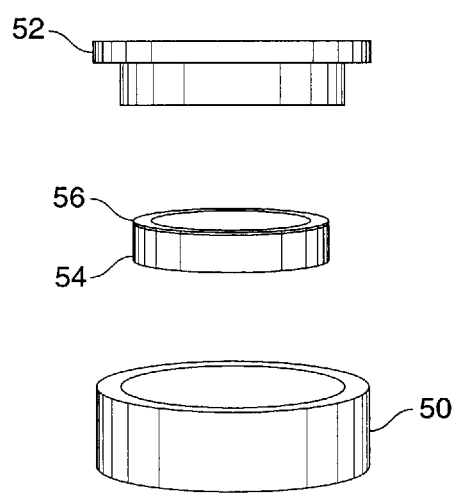
FIG. 9 is an exploded perspective view of an analysis vessel including a cap and a disk carrying an LCM film which may be disposed inside the vessel according to the present invention.
Figure 10A:
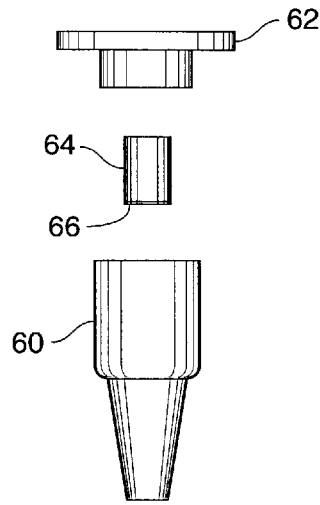
FIG. 10a is an exploded perspective view of an analysis vessel including a cap and a plug carrying an LCM film which may be disposed inside the vessel according to the present invention.
Figure 10B:
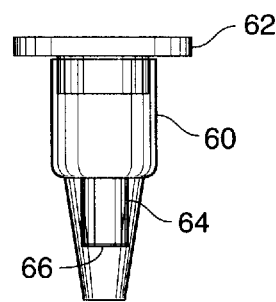
FIG. 10b is a side view of the analysis vessel of FIG. 10a showing the plug disposed inside the vessel according to the present invention.

FIGS. 9 and 10a and 10b illustrate embodiments of the present invention wherein the observation port may be located on the cap or may be located elsewhere on the vessel. Referring now to FIG. 9, an exploded perspective view is presented of an analysis vessel 50 including a cap 52 and a clear plastic disk 54 carrying an LCM film 56 which may be disposed inside the vessel 50 according to the present invention. The methods disclosed herein and other known methods may be used to affix LCM transfer film 56 to disk 54. A viewing port 58 may be provide at either the cap 52, the bottom of analysis vessel 50, or at both locations.

As will be appreciated by those of ordinary skill in the art, disk 54 has a shape which mates with the cross section of the interior of analysis vessel 50 and is sized for a slip fit such that it may be easily inserted therein but constrained from significant lateral motion once inside the analysis vessel 50.

Referring now to FIGS. 10a and 10b, yet another embodiment of the present invention is depicted. FIG. 10a is an exploded perspective view of an analysis vessel 60 including a cap 62 into which a plug 64 carrying an LCM transfer film 66 may be inserted according to the present invention. FIG. 10b is a side view of the analysis vessel of FIG. 10a showing the plug disposed inside the vessel according to the present invention. The LCM transfer film may be affixed to the surface of plug 64 as taught herein. A viewing port 68 may be provide at either the cap 62, the bottom of analysis vessel 60, or at both locations.

Those of ordinary skill in the art will appreciate that the embodiments of FIGS. 9, 10a and 10b may be used without the need for a solid cap for the analysis vessel. Techniques such as use of low vapor pressure oils are known for reducing evaporation of the liquid reagents used in LCM analysis and the present invention may be employed with such techniques.

Those of ordinary skill in the art will recognize that other orientations are contemplated according to the present invention, such as ones wherein the film is held in the analysis vessel in a fixed position with respect to a viewing port located at other positions on the analysis vessel. In general, the present invention provides in combination a LCM film mounted on a substrate which may be transparent if necessary for the particular application. While embodiments described herein comprise caps, disks and plugs, the substrate of the present invention is not limited to such particular forms. Because the LCM film is mounted in a fixed position on the substrate, it may be easily oriented with respect to other elements of an LCM tissue sample transfer device or analysis vessel.

As will be appreciated by those of ordinary skill in the art, the carrier comprising the substrate and mounted LCM transfer film of the present invention is easily used with apparatus for performing LCM tissue sample transfers. A plurality of substrates may be arranged according to the present invention to provide a degree of automation to the LCM process.

Figure 11:
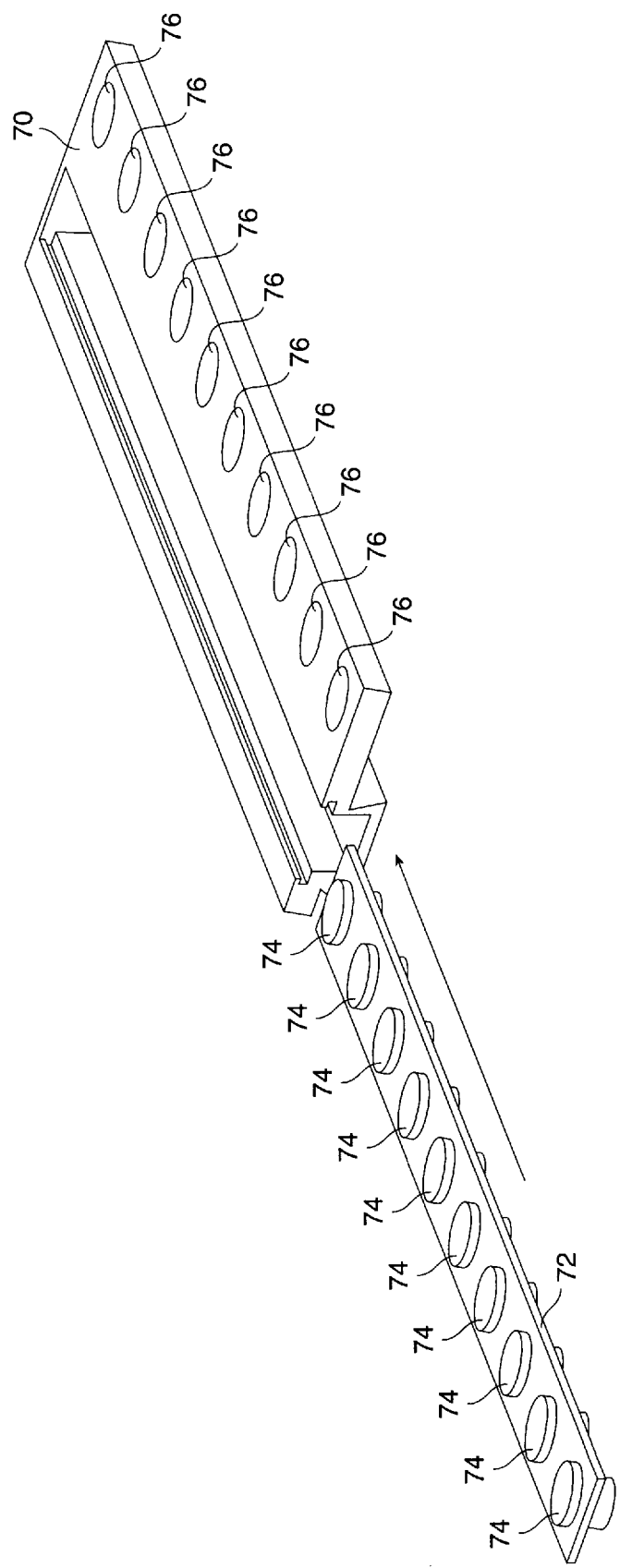
FIG. 11 is a diagram of a substrate carrier that slides into a mating mount which is indexed to precisely locate the position of the substrate relative to an element of an LCM tissue transfer apparatus.
Figure 12:
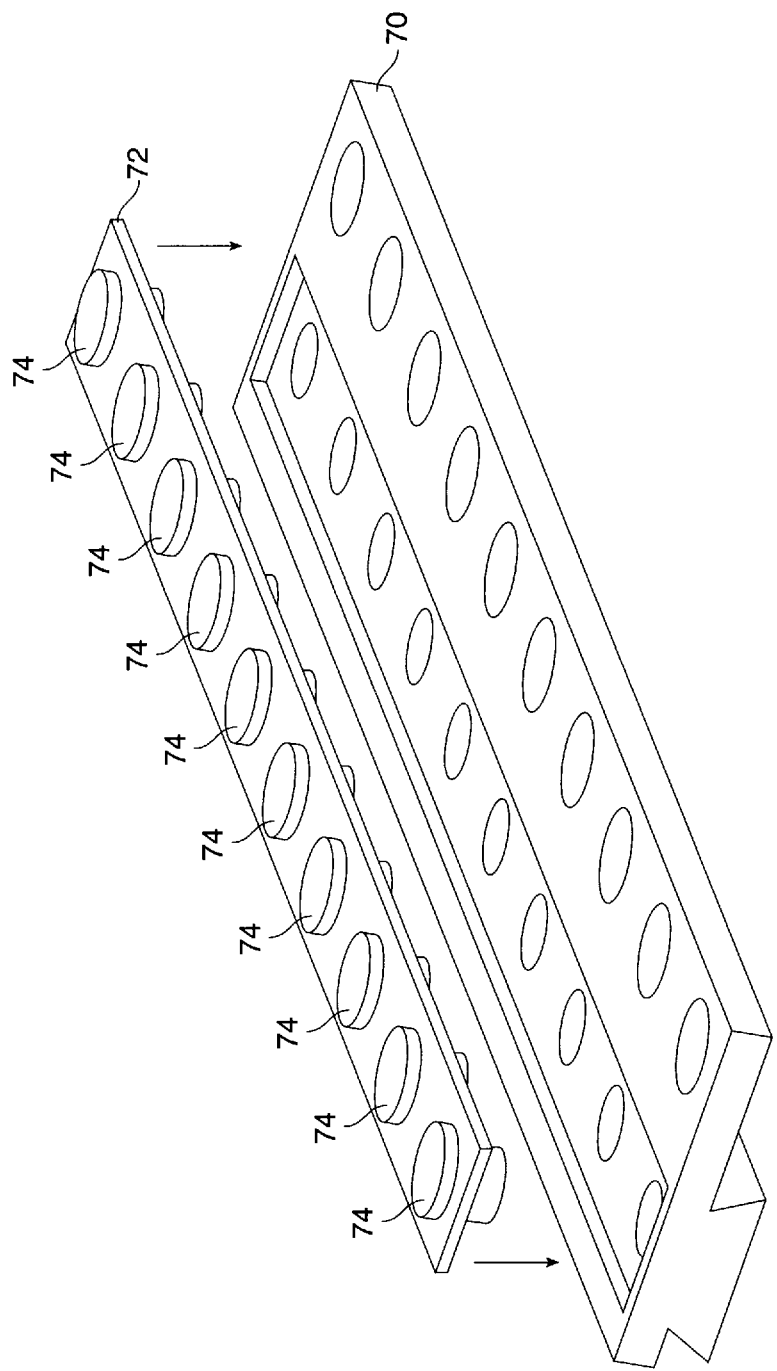
FIG. 12 is a diagram of an alternative method for mounting the substrate carrier.

Referring now to FOG. 11, a diagram is presented of a substrate carrier 70 that slides into a mating mount 72 which is indexed to precisely locate the position of the substrate relative to an element of an LCM tissue transfer apparatus. Many substrates can be evaluated in sequence by using a dovetail slide 70 which may be mounted to the side of the translation stages located on the microscope used in the LCM apparatus. This slide 70 can contain strip 72 holding a number of substrates 74 and vials in a parallel row of vial holder apertures 76 as indicated in FIG. 11. The dove tail slide can be indexed to provide precise locating of the substrates and vials to simplify loading and unloading. The substrates are contained in a plastic carrier that can be bar coded to provide a unique identification number for this set of substrates. The individual substrates can each be individually labeled on the top surface thereof as seen in FIG. 6 to provide a unique identifier. Since the top surface of the substrate 74, shown in FIG. 11 in the form of a cap, is several millimeters from the location of the transferred tissue the labels, will not effect the illumination or the viewing of the tissue sample because the label will be far from the focal plane of the imaging lenses and out of focus. FIG. 12 is a diagram of an alternative method for mounting the substrate carrier.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A laser capture microdissection sample vessel including;

a hollow body defining a volume therein;

a sealing means for mating with said hollow body at an aperture thereof and for sealing said volume;

an observation port disposed in one of said hollow body and said sealing means; and means for positioning a laser capture microdissection lift-off substrate in said sample vessel in a position observable from said observation port.

2. The laser capture microdissection sample vessel of claim 1 wherein said sealing means comprises a cap adapted to mate with the aperture of said sample vessel so as to seal said vessel.

3. A cap for sealing a laser capture microdissection sample vessel having an open end, said cap comprising:

a plastic member adapted to mate with the open end of said sample vessel so as to seal said sample vessel, said plastic member having a top surface and a bottom surface and further having an aperture formed from said top surface to said bottom surface; and a laser capture microdissection lift-off substrate mounted on said bottom surface across and sealing said aperture.

4. The cap of claim 3 having a thickness between said top surface and said bottom surface selected to be larger than the depth of field of a selected microscope objective, said cap further having a label on said top surface.

5. A cap for sealing a laser capture microdissection sample vessel having an open end, said cap comprising:

a plastic member adapted to mate with the open end of said sample vessel so as to seal said sample vessel, said plastic member having transparent optical quality windows on opposing top and bottom surfaces defining a solid volume thereof; and a laser capture microdissection lift-off substrate affixed to said window on said bottom surface.

6. The cap of claim 5 having a thickness between said top surface and said bottom surface selected to be larger than the depth of field of a selected microscope objective, said cap further having a label on said top surface.

* * * * *